United States Patent [19]

Heinecke

[11] Patent Number: 4,917,929
[45] Date of Patent: Apr. 17, 1990

[54] ONE PIECE ADHESIVE BANDAGE AND PACKAGE UNIT

[75] Inventor: Steven B. Heinecke, New Richmond, Wis.

[73] Assignee: Minnesota Mining and Manufacturing Company, St. Paul, Minn.

[21] Appl. No.: 298,628

[22] Filed: Jan. 18, 1989

[51] Int. Cl.⁴ .......................... B32B 7/06; B32B 7/12
[52] U.S. Cl. .......................................... 428/41; 428/40; 428/43; 428/121; 428/130; 128/155; 128/156
[58] Field of Search ................ 428/40, 42, 43, 130, 428/121, 41; 206/440, 441; 128/155, 156

[56] References Cited

U.S. PATENT DOCUMENTS

| 2,902,734 | 9/1959 | Walters | 428/40 |
|---|---|---|---|
| 3,018,881 | 1/1962 | Wall | 206/56 |
| 4,050,121 | 9/1977 | Richman | 24/73 VA |
| 4,127,132 | 11/1978 | Karami | 128/287 |
| 4,413,621 | 11/1983 | McCracken et al. | 128/156 |
| 4,513,739 | 4/1985 | Johns | 128/156 |
| 4,539,256 | 9/1985 | Shipman | 428/315.5 |
| 4,598,004 | 7/1986 | Heinecke | 428/40 |
| 4,614,183 | 9/1986 | McCracken et al. | 128/132 R |
| 4,781,293 | 11/1988 | Johns | 206/441 |
| 4,815,457 | 3/1989 | Mazars et al. | 128/155 |

Primary Examiner—Alexander S. Thomas
Attorney, Agent, or Firm—Donald M. Sell; Walter N. Kirn; Dale A. Bjorkman

[57] ABSTRACT

An adhesive composite is provided having a backing which is folded in such a way that no separate liner piece covering the adhesive is required. This invention provides an easily delivered one piece label, tape or dressing.

19 Claims, 2 Drawing Sheets

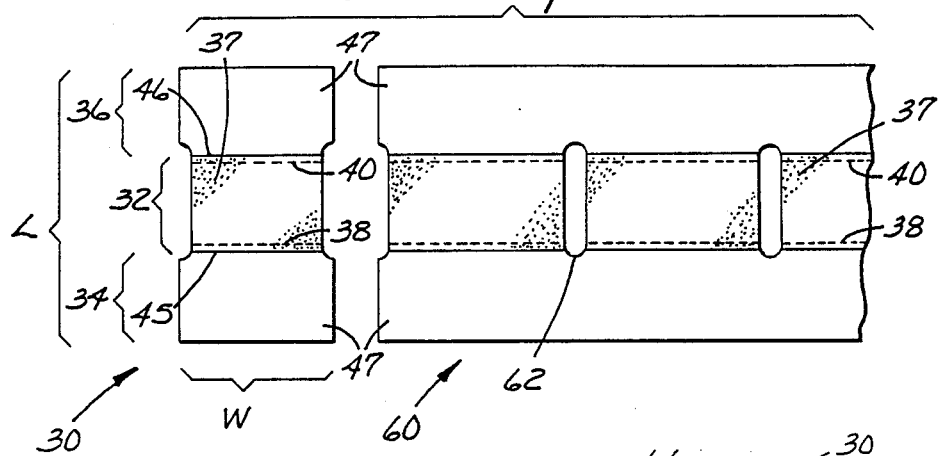
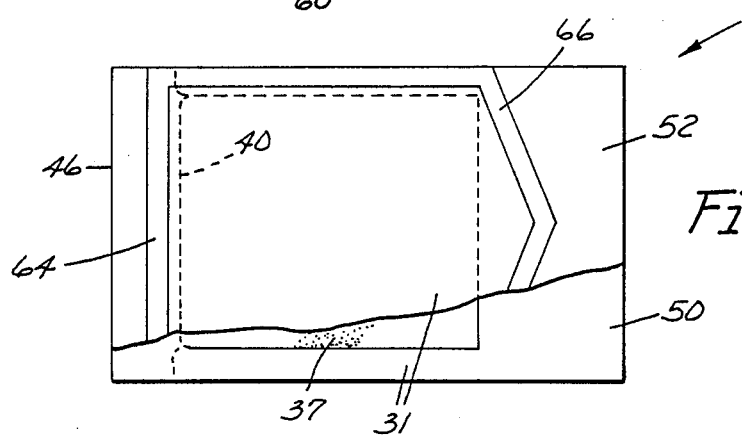
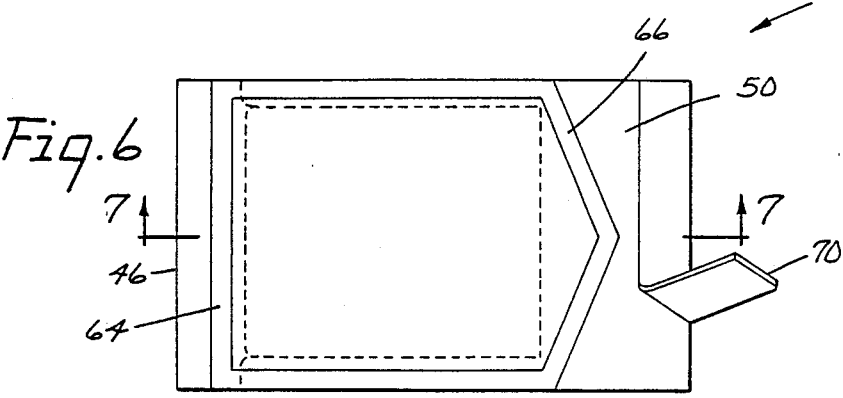
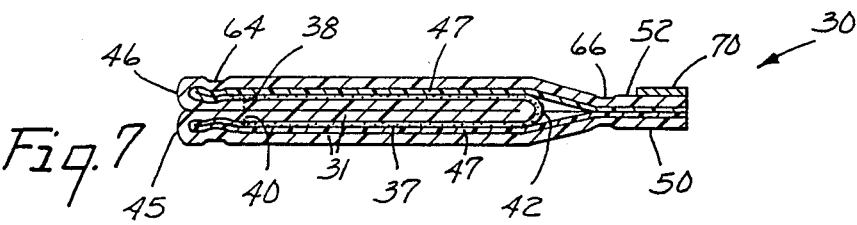

ONE PIECE ADHESIVE BANDAGE AND PACKAGE UNIT

FIELD OF INVENTION

The present invention relates to pressure-sensitive adhesive composites comprising a backing coated on one surface with adhesive. More particularly, it relates to pressure-sensitive adhesive composites having improved means for handling and application to a surface. The invention is of particular benefit in the application of backings which are very thin, adhesive-coated transparent films widely used as medical dressings.

BACKGROUND

Although the present invention is useful in any adhesive composite needing a delivery system, it has particular benefit in connection with transparent film dressings and surgical drapes. These dressings and drapes are widely used as a protective layer over a wound, facilitating healing in a moist environment while acting as a barrier to liquids and bacteria. Dressings of this type are available under trade names such as Tegaderm TM (3M, St. Paul, Minn.), Bioclusive TM (Johnson & Johnson, New Brunswick, N.J.), Op-Site TM (T.J. Smith & Nephew, Hull, England) and Uniflex TM (Howmedica, Largo, Fla.).

The polymeric films used in such dressings are conformable. By this it is meant that these films are extremely thin, flimsy, and supple. They are supplied with a releasable protective liner overlying the adhesive coated surface of the film. When the liner is removed, the adhesive coated film tends to wrinkle and stick to itself, interfering with the smooth aseptic application of the dressing or drape to the skin. Various delivery systems have been proposed to obviate this problem.

One such delivery system utilizes a three-part liner configuration. U.S. Pat. No. 4,614,183 describes a composite having a relatively thin polymeric film that is releasably adhered to two liner sections with a center gap between the liners. These two liner sections have short J-folds located next to the center gap. A third liner piece covers the center gap on the adhesive coated surface of the backing and extends beyond the J-folds for easy removal. To apply this dressing, the user must first remove the centerliner piece, apply the center region of the backing to the substrate, and then reach under the side portions of the dressing to grasp the J-folds and remove the liner pieces from the backing.

U.S. Pat. No. 3,018,881 discloses a folded adhesive bandage package unit having at least three liner pieces and where the adhesive-coated surface of the backing contacts the inside surface of the covering panels. This package has finger tabs that are pulled apart by the user, unfolding the bandage for application to the skin. The package forming panels are separated from the adhesive bandage after application to the skin by continued pulling of the finger tabs.

U.S. Pat. No. 4,598,004 discloses an adhesive composite having a backing coated with adhesive on at least a portion of the backing and a separate liner piece over the adhesive. At least one edge of the backing is a delivery strip which is securely adhered to the liner and which is separable from the remainder of the backing. The bond between the liner piece and the delivery strip on the backing is strong enough that the delivery strip will separate from the remainder of the backing before it will separate from the liner.

U.S. Pat. No. 4,050,121 discloses a linerless diaper tab which is folded around the diaper in a "Y configuration" to provide added strength in gripping the diaper. The portion of the tab that is used to fasten the diaper is wrapped around the edge of the diaper and releasably adhered to the anchoring portion of the tab for storage before use. U.S. Pat. No. 4,127,132 discloses a disposable diaper tape fastener wherein the tape tab is folded onto itself and may be unfolded two or more times to expose fresh adhesive. In at least one configuration, the tape strip is maintained in a folded configuration by a suitable means such as a spot of adhesive.

SUMMARY OF THE INVENTION

An adhesive composite is provided having a backing with a central region bounded on opposing sides by side regions. The central region has a pressure-sensitive adhesive coated on at least a portion of one face of the backing. This adhesive-coated face of the central region of the backing is releasably adhered to at least one of the side regions of the backing, providing an easily delivered one piece label, tape or dressing at a lower cost than previously available adhesive composites.

The adhesive composite may additionally comprise separation means for separating the central region of the backing from the side regions of the backing. Preferably, the separation means is a pair of parallel perforation lines provided in the backing so that after delivery of the composite to the substrate, the side regions are removed by tearing along the perforation lines.

In one configuration, the central region of the backing may be releasably adhered to only one of the side regions of the backing by folding the backing along a line generally within one of the side regions of the backing, this side region being sufficiently long that the adhesive-coated face of the central region is completely covered.

In a preferred embodiment, the central region of the backing is folded into two portions so that the non-adhesive coated faces of the portions are proximate or contact. This fold may be described as an "outward fold," because the adhesive coatings are on the outward facing surfaces of the folded central region of the backing. The backing is then folded again in each of the side regions, thereby releasably adhering the side regions of the backing to the corresponding adhesive coated face of the central region. This fold may be described as an "inward fold," because the adhesive coatings are on the inward facing surfaces of the folded backing.

The backing is preferably an adhesive coated film which is permeable to moisture and vapor and should transmit moisture vapor. When a high moisture vapor permeable film is used, the adhesives are preferably biocompatible. Most preferably the pressure-sensitive adhesive composite comprises high moisture vapor permeable film, a high moisture vapor permeable biocompatible adhesive and is transparent.

BRIEF DESCRIPTION OF DRAWINGS

FIG. 4 is a plan view of a method of preparation of the film dressing of FIG. 3.

FIG. 5 is a plan view of the film dressing of FIG. 3 which has additionally been heat sealed with some parts broken away to show layers.

FIG. 6 is a plan view of a dressing of FIG. 3 additionally comprising a label.

FIG. 7 is a cross-sectional view of the film dressing of FIG. 6 taken along the line 7—7.

DETAILED DESCRIPTION

Figure 2:
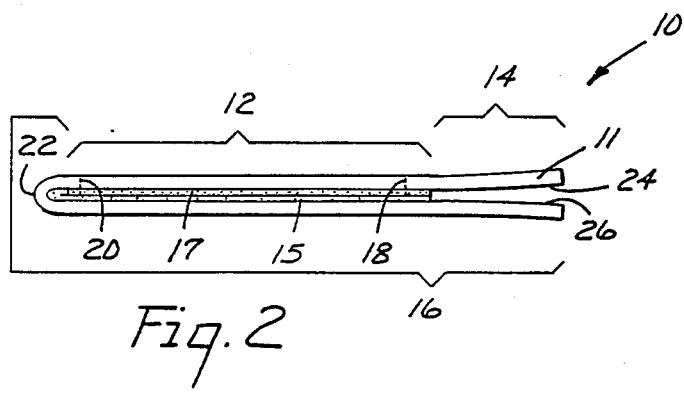
FIG. 2 is an edge view of a folded film dressing of FIG. 1.
Figure 1:
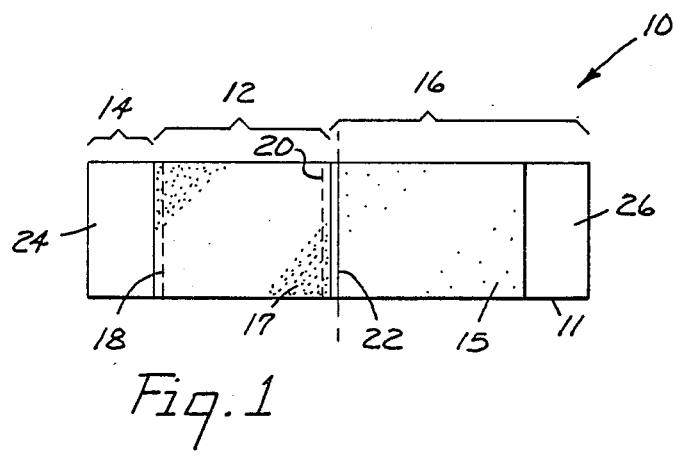
FIG. 1 is a plan view of an open or unfolded film dressing according to the present invention.

FIGS. 1 and 2 show dressing composite 10 of the present invention wherein like numerals refer to like parts of the embodiment. FIG. 1 shows a plan view of open or unfolded dressing 10, comprising backing 11 made of a thin, transparent polymeric film which is moisture vapor permeable and liquid and bacteria impermeable such as a polyester or polyurethane film. Backing 11 has central region 12 bounded on opposing sides by side region 14 and 16. Central region 12 is coated on one face with pressure-sensitive adhesive 17, which is an adhesive exhibiting low irritation to skin, preferably a hypoallergenic acrylate copolymer bioadhesive. Side region 16 is coated on one face with release material 15, which may be selected from low energy surface coating materials that reduce adhesion levels of adhesive to the backing, as indicated by the properties of the selected backing material and adhesive. In certain selections of backing material and adhesive, a release coating may not be necessary. Perforation lines 18 and 20 are provided to enable the separation of central region 12 from side regions 14 and 16 after delivery of the dressing to the skin. Central region 12 is releasably adhered to side region 16 by folding backing 11 along fold line 22.

FIG. 2 shows an edge view of the folded dressing embodiment of FIG. 1. In delivery of the composite, the user grasps non-adhesive coated ends 24 and 26 and pulls in radially opposite directions, thereby exposing the adhesive-coated face of central region 12. The user then applies central region 12 to the skin and separates side regions 14 and 16 from central region 12 by tearing along perforation lines 18 and 20.

Figure 3:
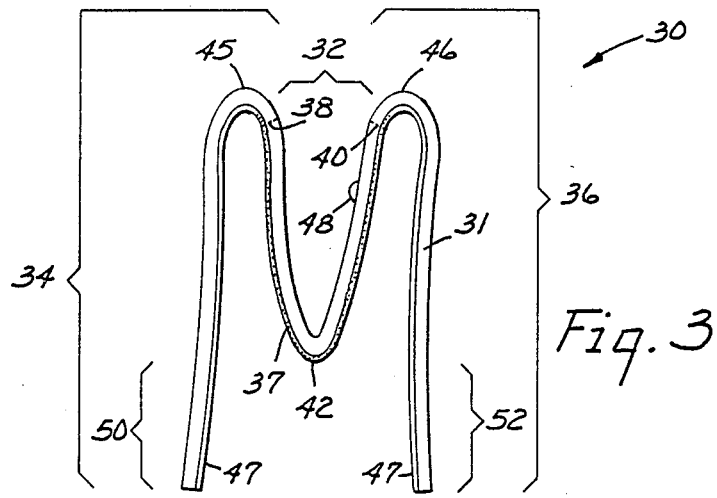
FIG. 3 is an expanded edge view of an alternative embodiment of a film dressing according to the present invention.

FIG. 3 is an expanded edge view of alternative dressing composite 30 of the present invention. In this embodiment, backing 31 has central region 32 and side regions 34 and 36. Adhesive 37 is coated on one face of central region 32. Perforation lines 38 and 40 are provided in central region 32 to allow for separation of central region 32 from side regions 34 and 36 after delivery of central region 32 to the skin. Preferably, adhesive 37 extends beyond perforation lines 38 and 40 so that after application, the part of dressing composite 30 that remains on the skin adheres around the edges of the dressing with no edge lift. Central fold 42 is provided in central region 32 and side folds 45 and 46 are provided in each of side regions 34 and 36, respectively, so that the adhesive-coated face of central region 32 is releasably adhered to side regions 34 and 36. In this three-fold embodiment, the non-adhesive coated faces of the portions of central region 32 on opposite sides of central fold 42 contact or are proximate. As yet another alternative embodiment, central fold 42 may be omitted, with side regions 34 and 36 abutting and having additional folds provided so that non-adhered ends 50 and 52 extend away from central region 32 and are available for easy grasp by the user. Backing association means 48, such as a dot or strip of adhesive, is located between the non-adhesive coated faces of the portions of central region 32 on either side of central fold 42 so that dressing composite 30 does not prematurely unfold and is easier to handle. In use, the user grasps non-adhered ends 50 and 52, one in each hand, and pulls in radially opposite directions. Through this action, the adhesive coated face of central region 32 is exposed and may be placed on the skin. After delivery of central region 32 to the desired location on the skin, side regions 34 and 36 are removed by tearing along perforation lines 38 and 40.

FIG. 4 shows a plan view of a method of preparation of the dressing embodiment of FIG. 3. In the preparation of dressing embodiment 30, backing sheet 60, optionally being wound from a roll, is provided with oblong shaped cutouts 62 located at regular intervals in backing sheet 60, so that after backing sheet 60 is partitioned into individual dressings, central region 32 is narrower in width than side regions 34 and 36. Backing sheet 60 is provided with parallel continuous perforation lines 38 and 40 which are preferably curved to provide rounded corners for the ultimately affixed dressing. Central region 32 of backing sheet 60 is coated with adhesive 37, and side regions 34 and 36 of backing sheet 60 are coated with release material 47. Although adhesive and release materials may be applied in any order, it may be found to be more convenient to coat the backing with release material first, followed by an overlapping coating of adhesive. Dressing embodiments 30 are partitioned from backing sheet 60 by die cutting along a line running longitudinally through oblong shaped cutouts 62. Dressing embodiment 30 may be folded while still in the form of sheet 60, or the dressings may be cut out first with subsequent folding of individual dressings. It will be appreciated that any of the forgoing steps may be interchanged with any of the other steps, resulting in essentially the same ultimate final product. Thus, for example, oblong shaped cutouts 62 could be supplied as a last step before folding.

FIG. 5 shows a plan view of a dressing of FIG. 3 with parts broken away to show layers, and additionally comprising a heat seal 64 around the periphery of the dressing and a first heat seal 66 which is recessed from the periphery, allowing the user to easily grasp non-adhered ends 50 and 52. As shown, heat seal 66 is chevron-shaped, but may be in any configuration that provides access to non-adhered ends 50 and 52. As an alternative to the use of heat seals 64 and 66, the edges of dressing 30 may be secured by means such as an adhesive.

FIG. 6 shows a plan view of the dressing embodiment of FIG. 3, additionally comprising a removable and optionally refixable label 70. Label 70 may be comprised of any relatively stiff material, such as paper or any of the materials appropriate for use as backing materials. In addition to providing a writing surface, label 70 is a reinforcement means that improves the handleability of dressing 30. Label 70 may be of any size that does not interfere with the delivery of dressing 30 to the skin. For example, label 30 may entirely cover side regions 34 and 36, extending to the edge of perforation lines 38 and 40. Label 70 may be releasably adhered to side regions 34 and 36 as a result of being the material onto which film backing 31 was extruded or cast, or may be releasably and refixably adhered to backing 31 by an adhesive.

FIG. 7 shows a cross-sectional view of the dressing of FIG. 6 taken along the line 7—7.

When extremely flimsy materials are used as the backing in adhesive composites of the present invention, the composite may be difficult to handle because the corners of the side regions may curl and the overall composite may tend to wrinkle. In these circumstances, it may be desirable to incorporate a reinforcement means particularly at the side regions to improve handleability. Such means may consist of, for example, elongated labels as described above, borders of paper or fiber, double thicknesses of liner in certain portions of the dressing, etc.

In the foregoing description it will be understood that the use of the terms "fold", "folded" and the like are used for convenience in designated parts of the composite and the relative spatial configurations of these parts. It will be apparent that actual creases in the backing and liner are not required to obtain the composite of this invention. However, the presence of actual creases in the backing is preferred.

The delivery system of the present invention is useful in connection with any backing having a pressure-sensitive adhesive coated on to it. Representative backings include non-woven fibrous webs, fibrous webs, knits, and other familiar backing materials. The preferred backing materials are polymeric films. The invention is particularly useful in pressure-sensitive adhesive composites having high moisture vapor permeable films. U.S Patent Nos. 3,645,835, and 4,595,001 both incorporated herein by reference, describe methods of making such a high vapor/moisture permeable film and methods for testing its permeability.

The film/adhesive composite should transmit moisture vapor at a rate of at least 300 g/m$^2$/24 hrs/37° C./100-10% RH. Preferably the adhesive coated film transmits moisture vapor at a rate of at least 700 g/m$^2$/24 hrs/37° C./100-10% RH.

The composite is preferably conformable to anatomical surfaces. This means that when the composite is applied to an animal anatomical surface it conforms to the surface even when the surface is moved. The preferred backings are also conformable to animal anatomical joints. When the joint is flexed and then returned to its unflexed position, the backing stretches to accommodate the flexion of the joint but is resilient enough to continue to conform to the joint when the joint is returned to its unflexed condition.

A measure of conformability is the "F" value, which is a measurement of force of elongation that is taken at a designated percent elongation point (identified by subscript) of a material. $F_{10}$ value as referred to herein is effectively determined using ASTM test method D 3759, except that the force measurements are taken at ten percent elongation. An Intelect II unit from Thwing-Albert Instrument Company (Philadelphia, Pa.) is used in this test procedure to obtain these values. The cross-head speed of the Intelect II is set at ten inches per minute and the chart speed is set at ten inches (25.4 cm) per minute. The gauge length is set at two inches (5.1 cm) with the test sample cut to test a one-inch width (2.54 cm).

The $F_{10}$ value gives an approximation of the motion of the body surface and ability of a material to stretch with these body deformations. The $F_{10}$ value for the backing should be no greater than about 1 pound (454 grams) and preferably less than about 0.8 pounds (363 grams). In the preferred embodiments of wound dressings and drapes, backings which have $F_{10}$ values upwards of 2.5 pounds (1135 grams) may be used. However, as the $F_{10}$ value increases, the conformability decreases and the ability of the backing to perform comfortably as medical dressings likewise decreases.

Conformability is also somewhat dependent on thickness, thus the thinner the backing the more conformable it is. Generally, the films are from 12 to 25 microns thick. Examples of polymers which are suitable for use as wound dressing films in the present invention include polyurethane such as Estane TM (B. F. Goodrich, Cleveland, Ohio), elastomeric polyester such as duPont Hytrel TM polyester elastomer (Wilmington, Del.), polyethylene, blends of polyurethane and polyester, chlorinated polyethylene, styrene/butadiene block copolymers such as Kraton TM brand thermoplastic rubber (Shell Chemical Company, Houston, Tex.), Pedax TM polyether block amides (distributed by Rilsan Corp., Glen Rock, N.J.), and polyvinyl chloride.

Preferred backings are polyurethane and elastomeric polyester films. These films combine the desirable properties of resiliency, high moisture vapor permeability and transparency. Particularly preferred backings are porous polyethylene films, which provide resiliency with even higher moisture vapor permeability than the polyurethane and elastomeric polyester films. Porous polyethylene and polypropylene films useful in the present invention are described in U.S. Pat. No. 4,539,256.

The porous polyethylene films as described above may additionally find usefulness as a liner material. Thus, in adhesive composites having a backing coated with an adhesive wherein the adhesive is covered by a liner and it is desirable to have a liner that is highly flexible and resilient, coated porous polyethylene or polypropylene films may ideally be used. Liners made from porous polyethylene or polypropylene are both highly conformable and possess great internal strength. These materials therefore resist bearding when peeled from an adhesive coated surface. Because these materials are capable of withstanding stresses in 180° peel angles and require only a very small amount of clearance at the point where the liner doubles back on itself, they provide particular usefulness as a liner material in applications where gradual and controlled peel is indicated. An example of such an application is automotive pinstriping tapes.

The preferred pressure-sensitive adhesives which can be used in the preferred wound dressing embodiment are the normal adhesives which are applied to the skin such as the acrylate copolymers described in Re. U.S. Patent No. 24,906, particularly a 97:3 iso-octyl acrylate:acrylamide copolymer. Other useful adhesives are those described in U.S. Pat. No. 3,389,827, which discloses block copolymers having three or more polymer block structures having a general configuration —A—B—A— wherein each A block is a thermoplastic polymer with a glass transition temperature above room temperature (i.e., above about 20° C.) having an average molecular weight between about 5000 and 125,000 and the B block is a polymer of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as, for example, those described in U.S. Pat. No. 4,112,213. Inclusion of medicaments or antimicrobial agents such as iodine in the adhesive is useful for enhancing wound healing and preventing infection. U.S. Pat. Nos. 4,310,509 and 4,323,557 describe such antimicrobial adhesives.

Various combinations of adhesives and release coatings are feasible. Those skilled in the art are familiar with processes of testing a new adhesive against different release coatings or a new release coating against different adhesives in order to arrive at the combination of qualities desired in the final product. Handbook of Pressure-Sensitive Adhesive Technology, Chapter 18 "Silicone Release Coatings" Van Nostrand-Reinhold, 1982, pp. 384–403 describes the considerations pertinent to selection of a silicone release liner. U.S. Pat. No. 4,472,480 describes considerations pertinent to selection of a perfluoropolyether release coating. In the preferred wound dressing embodiment of the present invention, the choice of adhesive is limited to those that are safe to use on skin, and preferably to those that are of the class known as hypoallergenic. The preferred acrylate copolymers are adhesives of this class.

While a low-adhesion backsize (LAB) may be appropriate for use in conjunction with a non-woven backing or with certain films, LAB's alone are generally not appropriate for use with porous polyethylene or polypropylene films. By altering the proportions of polydimethylsiloxane polymer, silicone resin, siloxane crosslinker and catalyst according to well known methods in the art, an appropriate silicone release coating can be prepared that possesses the desired release properties when used with the selected backing and adhesive. Radiation or thermally curable silicone materials are particularly suited to the preparation of release materials possessing the desired properties. The use of alternative release coating materials such as silicone/LAB blends will be apparent to the skilled artisan.

The composite of the present invention may be made by conventional techniques (e.g., extrusion, solvent casting, calendering, and laminating and the like) which are familiar to those skilled in the art. (See Modern Plastics Encyclopedia McGraw Hill, 1984-85; Coating and Laminating Machines, Weiss Coverting Technology Co., 1977.) The method of making a composite is further exemplified by the following non-limiting examples.

EXAMPLE 1

A sheet of porous polyethylene measuring 19 cm.×70 cm. with a thickness of 7.6 mm. (prepared according to example 23 of U.S. Pat. No. 4,539,256) was coated with a 7.3 cm. wide coating of adhesive, which was a 97:3 mixture of iso-octyl acrylate:acrylamide copolymer. A correspondingly sized liner piece was placed over the adhesive to protect the adhesive from contamination during subsequent preparation steps. The backing was coated with a 4.9 cm. wide strip of silicone release material on either side of the liner piece, which was an mixture of 95 parts of a polydimethylsiloxane polymer/catalyst mixture (commercially available from General Electric Company, Silicone Products Division, Waterford, N.Y. as SS4300), 5 parts of a silicone resin (commercially available from GE as SR545) and 2 parts of a crosslinking agent (commercially available from GE as 4300c). The release coating was cured by heat treatment at the comparatively low temperature of 65° C. for five minutes to avoid shrinkage of the backing.

Perforations were provided in the backing at the edge of the adhesive coating, assuring that the adhesive completely coated the area between the two perforation lines. At this time the protective liner piece was removed from the adhesive. The dressing was trimmed to size and the product was folded with an outward fold at the center and folded with inward folds in the side regions just outside of the perforation lines, thereby laminating half of the adhesive coated center region to each release surface coated side region.

EXAMPLE 2

An adhesive composition was prepared as in Example 1, except that the backing was a composite consisting of a non-woven backing and release material commercially available from Mead Release Products, West Chicago, Ill. (non-woven N7601-ST3A). The composite had a thickness of 0.15 mm. The center section bearing the release material was sanded to allow the applied adhesive to adhere to the backing.

EXAMPLE 3

An adhesive composite was prepared as in Example 1 except that a backing was prepared using an elastomeric polyester film (Hytrel TM, commercially available from duPont, Wilmington, Del.) and the release coating was a urethane low adhesion backsize.

EXAMPLE 4

An adhesive composite was prepared according to Example 3, except that the center region had a width of 6 cm., and the side regions had a width of 7 cm. The edges of the adhesive composite were heat sealed shut on all four sides, using a heat sealing machine Model 12AS from Packaging Industries, Inc.(Hyannis, Mass.). Thus a unitary package was provided.

EXAMPLE 5

An adhesive composite was prepared as in Example 4, except that the center region had a width of 5.5 cm. and the edges were sealed shut by a 4 mm. strip of a 97:3 mixture of iso-octyl acrylate:acrylamide copolymer adhesive rather than a heat seal.

The foregoing description has been directed to particular preferred embodiments for purposes of illustration and explanation. Those skilled in the art will appreciate that many modifications will be possible without departing from the spirit of the invention. For example, the composite may further comprise an absorbent pad or adhesive voids to increase moisture vapor transmission.

I claim:

1. An adhesive composite comprising a backing having a central region bounded on opposing sides by side regions, said central region having a pressure-sensitive adhesive coated on at least a portion of one face of the backing, and wherein said adhesive-coated face of said central region is releasably adhered to at least one of the side regions and wherein said central region is separable from the side regions by separation means.

2. The adhesive composite of claim 1 wherein said separation means is perforation lines provided in the backing.

3. The adhesive composite of claim 1 wherein said central region is releasably adhered to only one of the side regions.

4. The adhesive composite of claim 1 wherein said backing consists of porous polyethylene.

5. The adhesive composite of claim 1 wherein said backing consists of polyurethane.

6. The adhesive composite of claim 1 wherein said backing consists of a laminate of a film material and a web material.

7. The adhesive composite of claim 1 wherein said side regions are coated with a release material.

8. The adhesive composite of claim 2 wherein said release material comprises silicone.

9. The adhesive composite of claim 1 which additionally comprises a label releasably adhered to one of said side regions.

10. The adhesive composite of claim 1 which additionally comprises reinforcement means.

11. An adhesive composite comprising a backing having a central region bounded on opposing sides by side regions, said central region having a pressure-sensitive adhesive coated on at least a portion of one face of the backing, and wherein said adhesive-coated face of said central region is releasably adhered to two side regions.

12. The adhesive composite of claim 11 wherein said central region has a central fold so that the non-adhesive coated faces of portions of the central region on opposite sides of the central fold contact or are proximate.

13. The adhesive composite of claim 12 wherein the portions of the center region on opposite sides of the central fold are held together by a backing association means.

14. The adhesive composite of claim 13 wherein said backing association means consists of a strip of adhesive.

15. The adhesive composite of claim 12 wherein said backing is rectangular in shape having a length and a width, wherein said side regions and said central region are arranged along the length of the rectangular backing.

16. The adhesive composite of claim 15 wherein the width of said central region is narrower than the width of said side regions.

17. The adhesive composite of claim 16 wherein said composite is sealed around the periphery of the composite to form a unitary package.

18. The adhesive composite of claim 17 wherein said composite is heat sealed.

19. The adhesive composite of claim 17 wherein said composite is sealed with an adhesive.

* * * * *